(12) United States Patent
Christou (10) Patent No.: US 7,601,859 B2
(45) Date of Patent: Oct. 13, 2009

(54) ORGANOMETALLIC COMPLEXES

(75) Inventor: Victor Christou, Oxford (GB)

(73) Assignee: Isis Innovation Limited, Oxford (GB)

( * ) Notice: Subject to any disclaimer, the term of this patent is extended or adjusted under 35 U.S.C. 154(b) by 384 days.

(21) Appl. No.: 10/848,183

(22) Filed: May 18, 2004

(65) Prior Publication Data

US 2004/0215000 A1    Oct. 28, 2004

Related U.S. Application Data

(62) Division of application No. 09/445,050, filed as application No. PCT/GB98/01587 on Jun. 1, 1998, now abandoned.

(30) Foreign Application Priority Data

Jun. 2, 1997    (GB) ................................ 9711237.9

(51) Int. Cl.
C07F 5/00    (2006.01)
C07F 5/02    (2006.01)
C07D 293/00    (2006.01)
C07D 421/00    (2006.01)
C07D 517/00    (2006.01)
C07F 15/00    (2006.01)
C07D 231/00    (2006.01)
C07D 233/00    (2006.01)
C07D 235/00    (2006.01)
C07D 249/00    (2006.01)

(52) U.S. Cl. .................. 556/1; 556/7; 556/8; 548/100; 548/101; 548/110; 534/15; 534/16

(58) Field of Classification Search ................. 548/100, 548/101, 110; 556/1, 7, 8; 534/15, 16; 526/160
See application file for complete search history.

(56) References Cited

U.S. PATENT DOCUMENTS 5,237,069 A    8/1993    Newman
5,627,164 A *  5/1997    Gorun et al. .................. 514/64
5,707,745 A    1/1998    Forrest et al.

FOREIGN PATENT DOCUMENTS

WO    WO 93/11433    6/1993
WO    WO 98/06242    2/1998

OTHER PUBLICATIONS

Apostolidis et al. (Polyhedron, 16, 7, 1057-68, 1997.*
Sun et al. (Inorganic Chimica Acta 255, 355-360, 1997).*
Richter et al. (E J of Solid State and Inorganic Chemistry, 1996, 33, 10, 1063-69), (STIC/Abstract-attached) only.*
Takats (J of Alloys and Compounds, 249, 1997, 52-55).*
Liu et al. (Inorg Chem 1996, 35, 76-81).*
Maunder et al (Inorg Chem 1996, 35, 76-81).*
Chemical Physics Letters; vol. 276, No. 5-6; Armaroli et al., "Luminescence properties of Eu/sup 3+/, Tb/sup 3-/, and Gd/sup 3+/ Complexes of the Hexadentate N-donor Podand Tris-3-(2-pyridyl)pyrazol-1ylhydroborate"; Sep. 1997; pp. 435-440.
Jones et al., "Lanthanide Complexes of the Hexadentate N-donor Podand Tris [3-(2-pyridyl)pyrazoyl] hydroborate: Solid State and Solution Properties" Inorg. Chem, 1997, 36(1), 10-18.
Lawrence et al., "Heteroleptic Poly(pyrazoly)borate Derivatives of the Lanthanides. Structural and Electronic Spectral Studies of Somesalicylaldehyde Complexes", J. Chem. Soc., Dalton Trans. (1996), (4), 501-7.
Reger et al., "Luminescence Studies if Tris[dihydrobis(1-pyrazolyl)borato]terbium(III)", Inorg. Chem., (1991), 30(10), 2397-402.
Seminara et al., "Absorption and Emission Spectra of Neodymium(III) and Europium(III) Complexes", Inorg. Chem. Acta (1984), 95(6), 291-307.

* cited by examiner

Primary Examiner—Sreeni Padmanabhan
Assistant Examiner—Umamaheswari Ramachandran
(74) Attorney, Agent, or Firm—Volpe and Koening P.C.

(57) ABSTRACT

Organometallic complexes comprising a trivalent lanthanide metal ion complexed with one or more polydentate ligands containing one or more pyrazolyl-derived groups, such as trispyrazolyl borate species, are useful in light emitting materials e.g., in electroluminescent flat panel displays. In the complexes, several classes of which are novel, a coordinate bond is formed between the metal and one of the nitrogen atoms of the pyrazolyl rings.

3 Claims, 3 Drawing Sheets

ORGANOMETALLIC COMPLEXES

This invention relates to organometallic complexes, processes for their production, light emitting materials incorporating the complexes and light emitting devices comprising the complexes or the materials. The devices of the invention may be flat panel displays.

Flat panel displays are the critical enabling technology for many current applications, including laptop computers and "heads up" displays, as they offer several potential advantages over conventional cathode ray tube displays, including compactness and low power consumption.

Currently, the flat panel display market is dominated by liquid crystal technology, but these materials suffer several drawbacks including small operational viewing angles, poor image contrast and high power consumption. As an alternative technology for flat panel displays, electroluminescent displays using semiconducting organic polymers offer the potential of lower cost, improved viewing angles, better contrast and lower power consumption. However, these materials often have broad emission profiles, resulting in poor chromaticity and reduced device efficiency.

Typically, a flat panel device is a multilayer assembly of structurally important films consisting of a transparent electrode, insulation, phosphor and metal electrode. All are important materials in device fabrication, but the single most important element in the development of a multi-colour electroluminescent device is the phosphor.

It is known that organometallic complexes can be used as phosphors in electroluminescent devices. For example, U.S. Pat. No. 5,552,547 describes complexes of aluminium, gallium and indium in which one of the ligands acts as a "built-in" fluorescent dye. The colour of the light which is emitted from the complex is determined by the ligand which acts as the dye.

It has been suggested that lanthanide complexes can be used as phosphors in electroluminescent devices.

M. A. Pavier et al., Thin Solid Films, 284-285 (1996) 644-647, describe electroluminescence from dysprosium- and neodymium-containing Langmuir-Blodgett films. The ligand used in the complexes is a pyrazolone-based molecule in which the binding to the metal by the ligand occurs via a beta-diketonate-type arrangement.

The europium complex with phenanthroline and thenoyltrifluoroacetone is disclosed in Sano et al, *Jpn. J. Appl. Phys.*, vol. 34 (1995), p. 1883-1887 and Campos et al in *J. Appl. Phys.*, vol. 80, no. 12 (1996), p. 7144-7150. Both Sano et al and Campos et al teach the use of the complexes to provide red light in electroluminescent devices. Like the complexes disclosed by Pavier et al, it is the beta-diketonate part of the ligand which binds to the metal.

Campos et al mentions that fluorination of part of the beta-diketonate ligand imparts higher sensitising efficiencies to the complex. The sensitising efficiency of a complex is a measure of the efficiency of the process of energy transfer from the ligand to the metal during the excitation step associated with electroluminescence.

Fluorination of beta-diketonate ligands in organolanthanide complexes has been proposed as a way of shielding the metal ion from quenching by water molecules when the complexes are in aqueous solution; see Meshkova et al, *Sov. J. Coord. Chem.*, 18, 183 (1992). However, in most light emitting devices, metal complexes are either in the form of a thin film or are dispersed in a polymer matrix in the substantial absence of water molecules and so quenching of the metal ion does not occur by this mechanism. Therefore, the teaching of Meshkova et al, which is based on ensuring that water molecules cannot get close to the metal, is of little relevance to organometallic complexes for use in light emitting devices.

The present invention aims to provide organometallic complexes in which the metal is a lanthanide (i.e., organolanthanide complexes) which are more effective phosphors for use in light emitting devices than the known complexes.

The invention also seeks to provide a ligand system for organolanthanide complexes which is effective with a range of different lanthanides in order that the same ligand can provide radiation from different parts of the electromagnetic spectrum, e.g., red, green or blue light and UV or IR radiation, simply by varying the metal in the complex.

It is a further aim of the invention to improve the radiative efficiency of organolanthanide complexes. The radiative efficiency of an organometallic complex is a measure of the amount of energy which is radiated from the complex relative to the amount of energy lost via non-radiative pathways. The known organolanthanide complexes have the problem that a number of non-radiative pathways are available for energy loss from the metal and their radiative efficiencies can therefore be relatively low.

The present invention, in one embodiment, is based on the finding that pyrazolyl species are highly effective ligands for producing organolanthanide complexes useful as phosphors in light emitting devices. Accordingly, the invention provides a light emitting device comprising a complex containing a lanthanide metal cation complexed with from one to three polydentate ligands, wherein each ligand comprises one or more pyrazolyl groups, optionally substituted and optionally fused with a substituted or unsubstituted, heterocyclic or carbocyclic, aromatic or non-aromatic, ring system, one of the nitrogen atoms of the pyrazolyl groups forming a coordinate bond to the metal.

Preferably, the ligands are trispyrazolylborate anions, the pyrazolyl groups being optionally substituted and optionally fused with a substituted or unsubstituted, heterocyclic or carbocyclic, aromatic or non-aromatic, ring system, optionally substituted at the boron atom.

Suitable complexes for use in the invention are desirably those having the formula (I):

$$[(Z(L)_3)_pM]A_q \qquad (I)$$

wherein Z is a carbon atom or $R^1$—B fragment p is 1, 2 or 3 q is 3-p

A is a counterion $R^1$ is: (i) hydrogen, aryl or aralkyl each optionally substituted with from one to five halogen or $C_1$ to $C_8$ alkyl groups; or (ii) $C_1$ to $C_6$ alkyl, $C_1$ to $C_6$ alkenyl or $C_1$ to $C_6$ alkynyl each optionally substituted with one or more halogen atoms each L is covalently bound to Z and is independently selected from a group of the formula (II) or (III)

-continued (III)

in which $R^2$, $R^3$ and $R^4$ are independently selected from: (i) halogen, cyano, nitro, sulphono, amino, $C_1$ to $C_6$ alkylamino, $C_1$ to $C_6$ alkylamido, carboxyl, $C_1$ to $C_6$ alkyloxycarbonyl, hydroxy, $C_1$ to $C_6$ alkoxy, $C_1$ to $C_6$ alkylcarbonyloxy, $C_1$ to $C_6$ alkylcarbonyl $C_1$ to $C_6$ haloalkoxy and hydrogen; (ii) aryl or aralkyl each optionally substituted on the aryl ring or, for aralkyl, on the alkylene chain with from one or more of the groups mentioned under (i) above; and (iii) $C_1$ to $C_6$ alkyl, $C_1$ to $C_6$ alkenyl or $C_1$ to $C_6$ alkynyl each optionally substituted with one or more of the groups mentioned under (i) and (ii) above or either $R^2$ and $R^3$ or $R^3$ and $R^4$ are linked so as to form a fused, aromatic or non-aromatic, ring system with the pyrazolyl ring of L and M is a trivalent lanthanide metal ion. p is suitably 1 or 2 and is preferably 2.

The light emitting device of the invention may be a flat panel display.

The complexes of formula (I) in which $R^4$ and/or $R^2$ is —$(CX_2)_n X$ wherein n is 0 or a positive integer from 1 to 6 and X is halogen; or $R^4$ and/or $R^2$ is orthodihalogenated or orthodihalomethylated aryl, optionally further substituted on the aryl ring (e.g., with from one to three halogen atoms or $C_1$ to $C_6$ alkyl groups) or in which $R^2$ and $R^3$ or $R^3$ and $R^4$ are linked so as to form a fused, aromatic or non-aromatic, ring system with the pyrazolyl ring of L are believed to be novel and are also provided by the invention.

The term "alkyl" as used herein is intended to cover branched and unbranched $C_1$ to $C_6$ groups and alicyclic compounds for the $C_3$ to $C_6$ groups. The terms "alkenyl" and "alkynyl" are defined similarly with the only difference being that the groups may contain one or more unsaturated C=C bonds or C≡C bonds.

The term "aryl" covers $C_6$ to $C_{10}$ aromatic groups such as phenyl and naphthyl as well as heterocycles such as pyridyl, furyl and thiophenyl. The term "aralkyl" means $C_1$ to $C_3$ alkyl substituted with aryl, such as benzyl.

The term "halogen" means fluorine, chlorine, bromine or iodine. Of these, fluorine is the preferred halogen for the complexes of the invention.

Preferably, M is terbium (Tb), cerium (Ce), europium (Eu), erbium (Er), gadolinium (Gd), thulium (Tm), samarium (Sm) or neodymium (Nd). However, M may be another lanthanide metal such as praesodymium (Pr), for example. It will be appreciated that the metal is in the M (III) oxidation state in the complexes of the invention. The complexes with cerium, europium, erbium and gadolinium are preferred because they provide emissions of blue light, red light, IR radiation and UV radiation, respectively, and thus range across the electromagnetic spectrum. In electroluminescent devices, the complex with terbium unexpectedly gives blue light rather than the green light which is normally expected for terbium complexes. This is particularly advantageous since cerium complexes which are conventionally used to produce blue light have the problem of a relatively wide bandwidth for the emitted light. The terbium complex of the present invention emits blue light with a narrower bandwidth than the previously used cerium compounds and so provides an improved alternative source of blue light for light emitting devices.

The trispyrazolyl ligands used in the invention have been found to be particularly effective in terms of their sensitising efficiency i.e., in transferring energy to the metal in the excitation step of the light emitting (e.g., electroluminescence) process. They also impart high radiative efficiencies to the complexes by providing few non-radiative pathways for relaxation (i.e., energy loss from the metal in its excited state). The ligands have been reported. Dias et al, *Inorg Chem*, 1995, 34, 1975 and 1996, 35, 267 and Renn et al *Helv Chim Acta* (1995), 78, 993 describe the synthesis of the fluorinated trispyrazolyl borate ligands. Julia et al., Organic Preparations and Procedures International, 16, 299, 1984, discloses the preparation of the trispyrazolylmethane-derived ligands.

The complexes of the invention are generally called "organometallic" herein. However, it will be understood by those skilled in the art that this term is used synonymously with the term "coordination". Also, the term "complex" as used herein covers both neutral species and compounds containing a charged organolanthanide species as part of a complex salt.

The present invention is also based on the wider finding that non-radiative pathways for relaxation in organolanthanide complexes can be provided by carbon-hydrogen bonds in the ligand which are relatively close to the metal and the discovery that these pathways can be blocked by fluorinating the ligand to replace the carbon-hydrogen bonds by carbon-fluorine bonds or otherwise designing the ligand such that there are no carbon-hydrogen bonds within 5 Å, preferably 8 Å, more preferably 10 Å, of the metal centre (i.e., the centre of the metal atom). Therefore, in another embodiment, the invention provides light emitting material comprising an organometallic complex either as a film or dispersed within a matrix of a polymer, the organometallic complex being a complex wherein the ligands are optionally fluorinated and arranged about the metal such that there are no carbon-hydrogen bonds within 5 Å of the metal centre.

The light emitted from the light emitting devices of the invention may be produced by various mechanisms such as electroluminescence, photoluminescence or cathodoluminescence with electroluminescence being preferred.

The matrix is preferably of the type conventionally used in light emitting (e.g., electroluminescent) devices and based on polymer systems such as polyvinylcarbazole (PVK) or polymethylmethacrylate (PMMA) with a hole transporting material such as 2-(4-biphenylyl)-5-(5-tertbutylbenzene)-1,3,4-oxadiazole (BBO). The organolanthanide complexes used in the invention may themselves act as electron transporting materials, separately from or in addition to being a phosphor, in the light emitting devices.

The ligands $ZL_3$ used in the complexes of the present invention in which $R^4$ and/or $R^2$ is —$(CX_2)_n X$ or optionally substituted orthodihalogenated or orthodiperhalomethylated aryl are particularly advantageous for use in the electroluminescent material of the invention since they provide complexes with no carbon-hydrogen (C—H) bonds within 5 Å of the metal centre. However, it will be appreciated that other ligands can achieve the same effect and thus also block the non-radiative pathways for relaxation. It is notable that in all of the known complexes for use in matrices in light emitting devices mentioned above, carbon-hydrogen bonds are available for non-radiative relaxation.

In the complexes of the invention, $R^4$ and/or $R^2$ is conveniently trifluoromethyl. $R^3$ may be hydrogen and $R^2$ trifluoromethyl. Alternatively, $ZL_3$ may be:

The increased conjugation of the fused bi- and poly-cyclic systems can be advantageous for electron transfer within the complex.

Where the complexes used in the invention are positively charged, they will be provided by compounds containing the complex and a counterion. The counterion preferably should not provide non-radiative pathways for relaxation of the metal. Therefore, it is preferred that the counterion should not contain bonds between hydrogen and other atoms, such as carbon-hydrogen bonds. Trifluoromethylsulphonate, $CF_3SO_3^-$, halide (fluoride, chloride, bromide or iodide), nitrate, $NO_3^-$, and perchlorate, $ClO_4^-$, are suitable counterions for this purpose.

In yet another embodiment, the present invention provides a process for producing the complex of the invention which comprises the steps of reacting $M^{3+}$ ions (i.e., trivalent lanthanide ions) with $ZL_3$ anions in solution and separating the complex from the reaction mixture. The process is carried out in a suitable solvent at about or above room temperature up to the boiling point of the solvent for a time sufficient to form an extractable amount of the complex, preferably with stirring.

Preferably, the complex is separated from the reaction mixture by solvent extraction. To avoid the presence of water molecules in the complex which might provide non-radiative relaxation pathways, the process is preferably carried out under anhydrous conditions. It is also advantageous to exclude oxygen from the reaction mixture by carrying out the process under an inert gas atmosphere e.g., of nitrogen or argon.

The process may be carried out via the following reaction:

$$pM'ZL_3 + MA_3 \rightarrow (ZL_3)_pMA_q + pM'A$$

wherein M' is a monovalent metal such as an alkali metal e.g., sodium or potassium, or thallium or silver (as $Tl^+$ and $Ag^+$, respectively)

p, M, Z and L are as defined above, and q is 3-p and A is a counterion.

In a preferred version of the process, two equivalents of $M'ZL_3$ are suspended or dissolved in a solvent and are treated with one equivalent of a trivalent lanthanide salt. The reaction mixture is stirred for a period of time between one and 100 hours either at room temperature or at the boiling point of the solvent under standard conditions. The solvent is removed (for example, by evaporation under reduced pressure) and the complex separated from by-products by extraction into a solvent with a different polarity from that of the reaction solvent. The product is purified by crystallisation from either the extraction solvent or a combination of solvents with different polarities.

The invention is illustrated, by way of non-limiting example only, by reference to the drawings in which.

Figure 1:
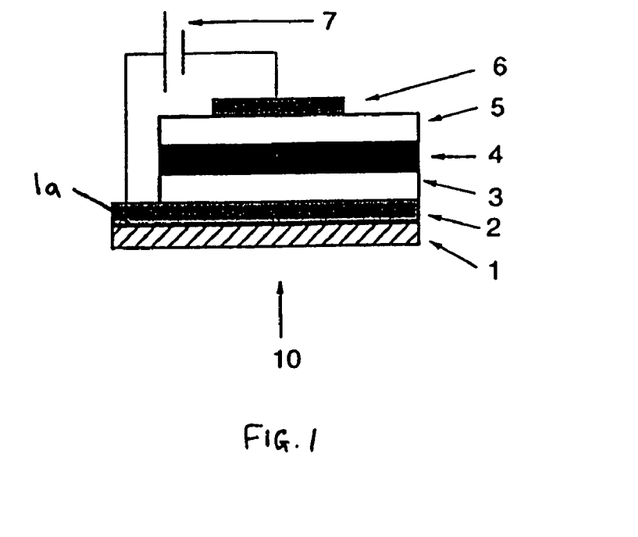
FIG. 1 shows a simplified cross-sectional view of an electroluminescent device according to the invention, such as an organic flat panel display.

The device 10 of FIG. 1 includes a substrate 1 which generally has a substantially planar surface 1a and may be a glass plate, although other suitable materials can be used for this purpose. An electrically conductive layer 2 is deposited on the planar surface 1a so as to form a relatively uniform electrical contact. Layers 3, 4 and 5 may be a single layer (for example, of the electroluminescent material of the present invention) comprising a mixture of conductive materials and luminescent dopant (such as a complex of the invention). However, it is known that this results in reduced device efficiency and a more efficient working device consists of a first organic layer 3 of a hole transporting material, the host emissive material 4 (such as the electroluminescent material of the invention), a second organic layer 5 of electron transporting material (which may comprise an organolanthanide of the invention also useful as a phosphor) and a second electrically conductive layer 6 to form a second electrical contact.

It will be appreciated that light generated within the host emissive material 4 can be emitted either through first organic layer 3, conductive layer 2 and substrate 1 or through second organic layer 5 and second conductive layer 6. In the device 10 depicted in FIG. 1, substrate 1 is formed of glass and conductive layer 2 is formed of organic and inorganic conductors, such as conductive polyaniline (PANI) or indium-tin-oxide (ITO), which are substantially transparent to visible light so that the emitted light exits downwardly through substrate 1 as the device 10 is shown in the Figure.

Device 10 has a potential applied between layers 2 and 6 by means of a potential source 7. In the embodiment of the invention shown in the Figure, conductive layer 2 is a p-type contact and conductive layer 6 is an n-type contact. The negative terminal of potential source 7 is connected to conductive layer 6 and the positive terminal is connected to conductive layer 2. Electrons injected through the n-type contact are transported through organic layer 5 and into organometallic layer 4 (the emissive layer). Holes injected from the p-type contact are transported through the organic layer 3 and into the organometallic layer 4 where, upon an electron and hole recombination, a photon is emitted.

The invention will now be further described by the following examples which are not intended to limit the scope of the invention in any way. In the examples, $Tf=CF_3SO_3^-$ and

EXAMPLE 1

[Ce(Bpz)$_2$(OTf)]

Figure 5:
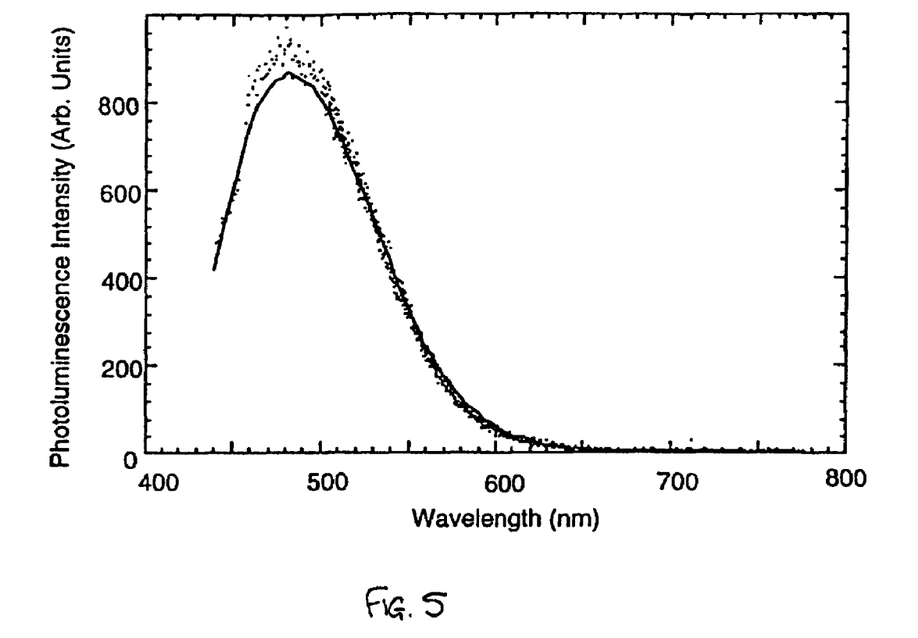

A mixture of Ce(OTf)$_3$ (1.0 g, 1.65 mmol) and KBpz (1.1 g, 3.31 mmol) in THF (100 mL) were stirred at room temperature, under N$_2$. The solution gradually became yellow over 1 h. The mixture was left to stir for a further 14 h and the THF was then removed under reduced pressure to give a yellow residue. The product was extracted from the yellow residue with CH$_2$Cl$_2$ (50 mL). Subsequent removal of the CH$_2$Cl$_2$ in vacuo afforded the product as a pale yellow solid (0.69 g, 47%). A photoluminescence plot for this complex is shown in FIG. 5.

EXAMPLE 2

[Tb(Bpz)$_2$(OTf)]

Figure 4:
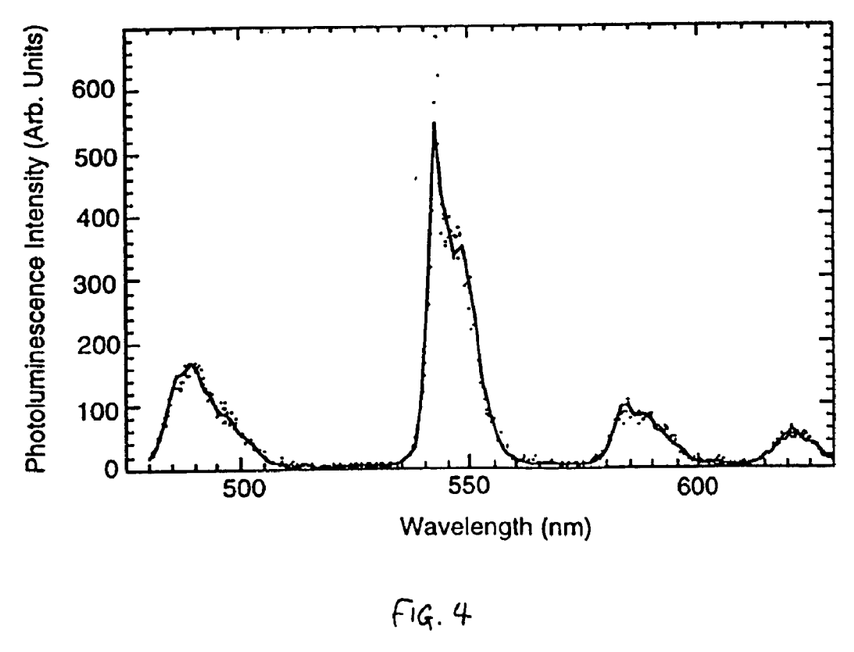

A mixture of Tb(OTf)$_3$ (1 g, 1.65 mmol) and KBpz (1.1 g, 3.31 mmol) in THF (100 mL) was allowed to stir for 14 h. During this time a colourless precipitate formed. The THF was removed under reduced pressure, the colourless residue treated with CH$_2$Cl$_2$ (2×50 mL) and the supernatant filtered. Removal of the CH$_2$Cl$_2$ under reduced pressure gave the product as a colourless microcrystalline solid (0.87 g, 58%). A photoluminescence plot for this complex is shown in FIG. 4.

Figure 2:
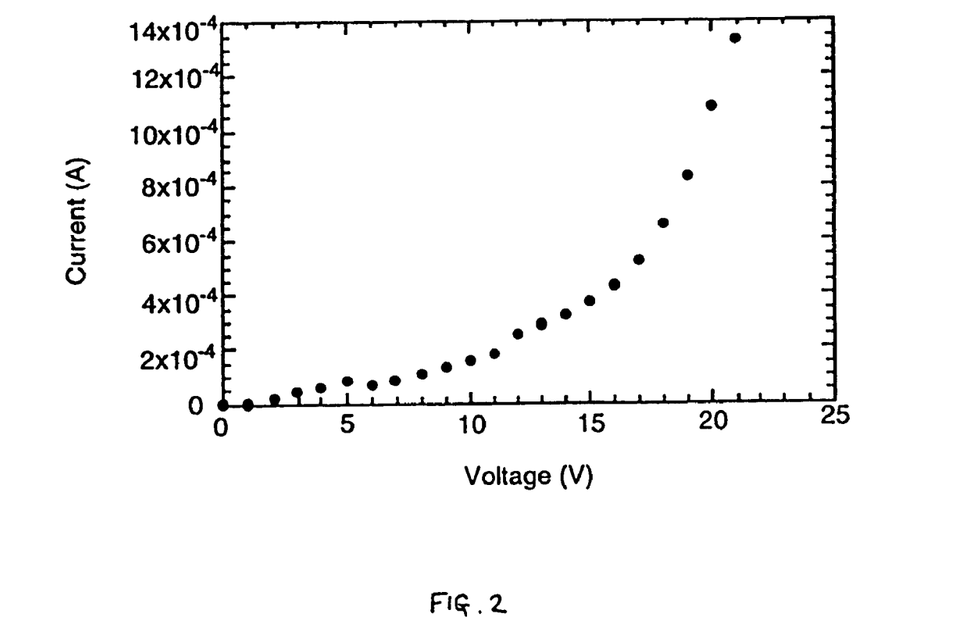
FIG. 2 is a current versus voltage plot for an electroluminescent device according to the invention.
Figure 6:
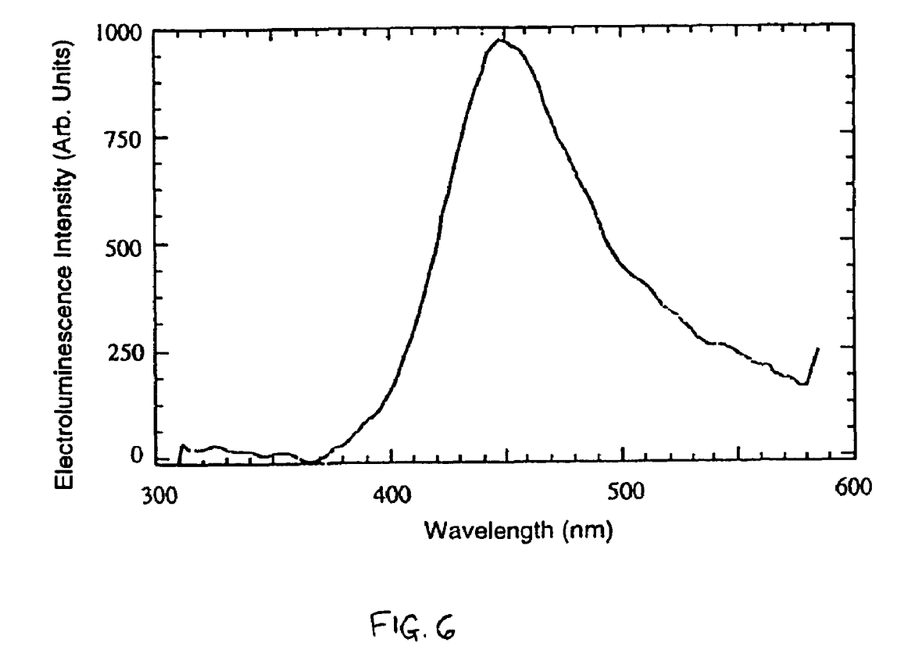
FIG. 6 is a plot of electroluminescence intensity versus wavelength for an electroluminescent device of the invention containing a terbium complex of the invention.

An electroluminescent device was prepared using this complex as a phosphor. The device had a single layer structure consisting of a homogeneous mixture of the organometallic phosphor, an electron carrying material and a hole carrying material. This layer was deposited by spin-coating a stock solution of these materials onto an indium-tin oxide coated glass substrate in a dry nitrogen atmosphere. The stock solution was prepared in a dry nitrogen atmosphere using a mixture of the organometallic phosphor, polyvinylcarbazole (PVK) and 2-(4-biphenylyl)-5-(5-tertbutylbenzene)-1,3,4-oxadiazole (BBO). This solid mixture was then dissolved in THF to give a solution having the following concentrations: [Tb(Bpz)$_2$(OTf)], 4.0 gdm$^{-3}$; PVK, 20.0 gdm$^{-3}$; BBO, 20.0 gdm$^{-3}$. The counter electrode consisted of a magnesium contact overcoated with aluminium. A current versus voltage plot for the device is shown in FIG. 2 and an electroluminescence intensity versus wavelength plot is shown in FIG. 6.

EXAMPLE 3

[Eu(Bpz)$_2$(OTf)]

Figure 3:
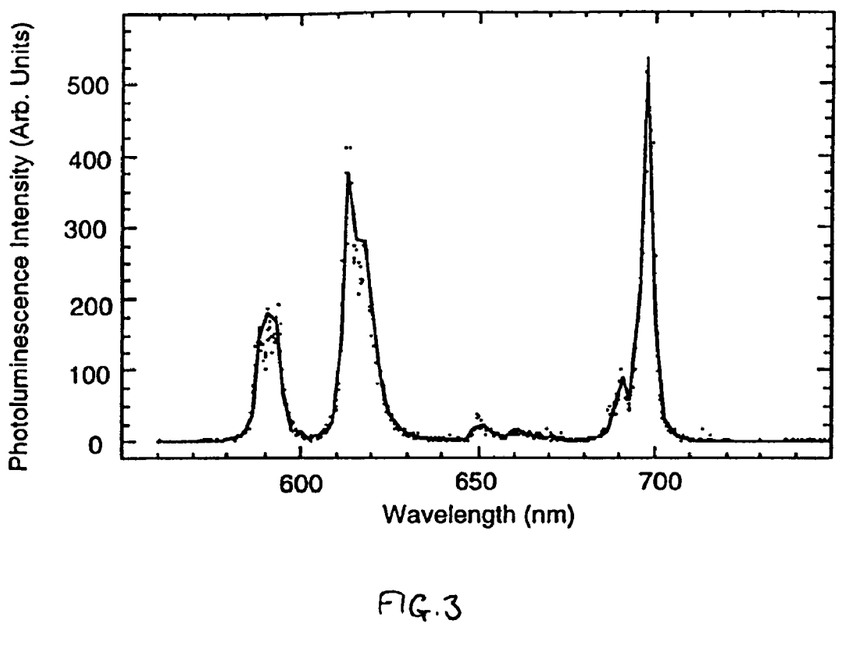
FIGS. 3, 4 and 5 are photoluminescence plots for europium, terbium and cerium complexes of the invention.

A mixture of Eu(OTf)$_3$ (1 g, 1.67 mmol) and KBpz (1.11 g, 3.30 mmol) was suspended in THF (100 mL) and the mixture stirred at room temperature for 12 h. A fine pale precipitate formed after 1 h and the solution became pale yellow in colour. The THF was removed in vacuo and the product was extracted from the resulting pale yellow solid with CH$_2$Cl$_2$ (2×50 mL). Evaporation of the CH$_2$Cl$_2$ under reduced pressure gave the product as a pale yellow powder (1.16 g, 78%). A photoluminescence plot for this complex is shown in FIG. 3.

EXAMPLE 4

[Er(Bpz)$_2$(OTf)]

Er(OTf)$_3$ (2 g, 3.25 mmol) and KBpz (2.19 g, 6.51 mmol) were mixed together under N$_2$ and THF (100 mL) was added. A fine colourless precipitate formed during the first 1 h of the reaction, whilst the solution remained a pale pink colour. This mixture was left to stir for 12 h overnight and then the THF was removed under reduced pressure. The pale pink product was extracted from the residue with CH$_2$Cl$_2$ (2×50 mL) and isolated as a powder by evaporation of the solution under reduced pressure (2.46 g, 83%).

EXAMPLE 5

[Eu(Bpz)$_2$(Cl)]

EuCl$_3$ (1 g, 3.87 mmol) and KBpz (2.6 g, 7.82 mmol) were mixed together under N$_2$ and THF (100 mL) was added. The resulting mixture was stirred for 1 h, by which time the solution had changed colour to orange and a fine colourless precipitate had formed. This mixture was left to stir for 14 h and then the THF was removed in vacuo. The product was extracted from the resulting pale yellow solid with CH$_2$Cl$_2$ (2×50 mL) and the resulting solution was then evaporated to dryness giving a pale yellow powder. This powder was washed with hexane (50 mL) and recrystallised from hot toluene to give the product as a yellow solid (0.48 g). A second crop of crystals (0.87 g) was obtained by concentrating the toluene supernatant (1.35 g, 45%).

EXAMPLE 6

[Eu(Bpf)$_2$Cl]

KBpf

A mixture of pf[H] (2.57 g, 12.6 mmol) and KBH$_4$ (0.12 g, 2.2 mmol) were suspended in dry decalin (20 mL) and the mixture was heated to 250° C. After 4 h the mixture was cooled to room temperature and the pale yellow decalin solution filtered from the colourless sticky residue. The residue was triturated with pentane (50 mL), the pentane removed by filtration and the residue dried under reduced pressure to give the product as a colourless powder (0.62 g, 42%).

Eu(OTf)$_3$ (0.257 g, 0.43 mmol) and KBpf(DMAC) (0.64 g, 0.86 mmol) were mixed under nitrogen and THF (100 mL) was added dropwise to the mixture at room temperature. After 26 hours, the THF was removed by vacuum and the product extracted from the resulting orange oil with THF (100 mL). The product was recovered from the THF solution as a pale brown solid by precipitation after concentration of the solution to 10 mL followed by addition of a large volume of hexanes (500 mL). The solid was dried under dynamic vacuum at room temperature for 4 hours.

Yield: 0.36 g (54%)

EXAMPLE 7

Tm(Bpz)$_2$(OTf)

A mixture of Tm(OTf)$_3$ (0.62 g, 1.0 mmol) and KBpz (0.67 g, 2.0 mmol) were dissolved in THF (50 mL) and the solution was stirred for 12 h at room temperature. A fine colourless precipitate developed within 1 h. After 12 h the THF was removed under vacuum and the product extracted from the resulting colourless solid with CH$_2$Cl$_2$ (50 mL). Removal of the CH$_2$Cl$_2$ in vacuo afforded the product as a colourless solid (0.72 g, 79%).

EXAMPLE 8

Sm(Bpz)$_2$(OTf)

A mixture of Sm(OTf)$_3$ (1.97 g, 2.0 mmol) and KBpz (1.33 g, 4.0 mmol) were dissolved in THF (50 mL) and the solution was stirred for 48 h at room temperature. The THF was then removed under vacuum and the product extracted from the resulting colourless solid with CH$_2$Cl$_2$ (50 mL). Removal of the CH$_2$Cl$_2$ in vacuo afforded the product as a colourless solid (1.59 g, 89%).

EXAMPLE 9

Gd(Bpz)$_2$(OTf)

A mixture of Gd(OTf)$_3$ (1.21 g, 2.0 mmol) and KBpz (1.33 g, 4.0 mmol) in THF (50 mL) was stirred for 20 h at room temperature. The solvent was removed under reduced pressure and the product extracted from the solid residue with CH$_2$Cl$_2$ (50 mL). Evaporation of the CH$_2$Cl$_2$ under reduced pressure gave the product as a pale yellow solid (1.29 g, 62%).

EXAMPLE 10

Nd(Bpz)$_2$(OTf)

A mixture of Nd(OTf)$_3$ (1.18 g, 2.0 mmol) and KBpz (1.33 g, 4.0 mmol) were dissolved in THF (50 mL) and the purple solution was stirred for 24 h at room temperature. A fine colourless precipitate developed within 1 h. After 24 h the solution was pink. The solvent was removed under vacuum and the product extracted from the resulting colourless solid with CH$_2$Cl$_2$ (50 mL). Removal of the CH$_2$Cl$_2$ in vacuo afforded the product as a purple solid (1.36 g, 77%).

EXAMPLE 11

Ce(T$_{Ind}$)$_2$(OTf)

A mixture of Ce(OTf)$_3$ (0.59 g, 1.0 mmol) and KT$_{Ind}$ (0.81 g, 2.0 mmol) in THF (50 mL) was stirred at room temperature under N$_2$ for 20 h. The THF was removed under reduced pressure to give a yellow residue. The product was extracted from the yellow residue with CH$_2$Cl$_2$ (50 mL). Removal of the CH$_2$Cl$_2$ in vacuo afforded the product as a pale yellow solid (0.55 g, 54%).

EXAMPLE 12

Tb(T$_{Ind}$)$_2$(OTf)

A mixture of Tb(OTf)$_3$ (0.61 g, 1.0 mmol) and KT$_{Ind}$ (0.81 g, 2.0 mmol) in THF (50 mL) was allowed to stir for 16 h, by which time a colourless precipitate had formed. The THF was removed under reduced pressure and the pale yellow residue was treated with CH$_2$Cl$_2$ (50 mL) and the yellow supernatant filtered from the colourless precipitate. Removal of the CH$_2$Cl$_2$ under reduced pressure gave the product as a pale yellow solid (0.71 g, 69%).

EXAMPLE 13

Eu(T$_{Ind}$)$_2$(OTf)

A mixture of Eu(OTf)$_3$ (0.60 g, 1.0 mmol) and KT$_{ind}$ (0.81 g, 2.0 mmol) in THF (50 mL) was stirred for 20 h at room temperature. The solvent was removed under reduced pressure and the product extracted from the solid residue with CH$_2$Cl$_2$ (50 mL). Evaporation of the CH$_2$Cl$_2$ under reduced pressure gave the product as a pale yellow solid (0.59 g, 57%).

EXAMPLE 14

Tm(T$_{Ind}$)$_2$(OTf)

Tm(OTf)$_3$ (0.62 g, 1.0 mmol) and KT$_{ind}$ (0.81 g, 2.0 mmol) were dissolved in THF (50 mL) and the orange solution was stirred for 15 h at room temperature. The solvent was removed from the resulting cloudy solution and the yellow residue was washed with CH$_2$Cl$_2$ (50 mL). The yellow filtrate was evaporated to dryness under reduced pressure, affording the product as a pale yellow solid (0.68 g, 65%).

EXAMPLE 15

Sm(T$_{Ind}$)$_2$(OTf)

Sm(OTf)$_3$ (0.60 g, 1.0 mmol) and KT$_{ind}$ (0.81 g, 2.0 mmol) were dissolved in THF (50 mL) to give an orange cloudy solution. This mixture was stirred for 48 h and the solvent removed under reduced pressure. The product was isolated from the resulting yellow solid by extraction into CH$_2$Cl$_2$ and then removal of the solvent under reduced pressure (0.731 g, 72%).

EXAMPLE 16

Gd(T$_{ind}$)$_2$(OTf)

Gd(OTf)$_3$ (1.21 g, 2.0 mmol) and KT$_{ind}$ (1.61 g, 4.0 mmol) were dissolved in THF (50 mL) to give a cloudy yellow solution. This mixture was stirred for 16 h and then the solvent was removed. The product was extracted from the yellow residue with CH$_2$Cl$_2$ (50 mL) and isolated as a pale yellow powder upon removal of the CH$_2$Cl$_2$ in vacuo (1.59 g, 77%)

EXAMPLE 17

Nd(T$_{Ind}$)$_2$(OTf)

Nd(OTf)$_3$ (1.18 g, 2.0 mmol) and KT$_{ind}$ (1.61 g, 4.0 mmol) were dissolved in THF (50 mL) and the lilac solution was stirred for 24 h at room temperature. The solvent was removed from the resulting cloudy solution and the lilac residue was washed with CH$_2$Cl$_2$ (50 mL). The lilac filtrate was evaporated to dryness under reduced pressure, affording the product as a lilac solid (1.27 g, 62

EXAMPLE 18

Tb(Bpz$^{12}$)$_2$(OTf)

Tb(OTf)$_3$ (1.21 g, 2.0 mmol) and KBpz$^{12}$ (2.23 g, 4.0 mmol) were suspended in THF (50 mL) and allowed to stir for 14 h. The initial colourless cloudy mixture cleared and became pale green during this time. The solvent was removed under reduced pressure and the colourless solid residue was extracted into CH$_2$Cl$_2$ (50 mL). The filtrate was concentrated to dryness to give the product as a colourless solid (2.00 g, 74%).

EXAMPLE 19

Ce(Bpz$^{12}$)(OTf)$_2$

Ce(OTf)$_3$ (1.17 g, 2.0 mmol) and KBpz$^{12}$ (2.23 g, 4.0 mmol) were suspended in THF (50 mL) and allowed to stir for 14 h. The initial colourless cloudy mixture cleared during this time. The solvent was removed under reduced pressure and the colourless solid residue was extracted into CH$_2$Cl$_2$ (50 mL). The filtrate was concentrated to dryness to give the product as a pale yellow/green solid (1.59 g, 83

EXAMPLE 20

Eu(Bpz$^{12}$)$_2$(OTf)

Tb(OTf)$_3$ (1.20 g, 2.0 mmol) and KBpz$^{12}$ (2.23 g, 4.0 mmol) were suspended in THF (50 mL) and allowed to stir for 14 h. The initial colourless cloudy mixture cleared and became yellow during this time. Analysis of the product at this time showed only 1 ligand coordinated to the metal centre The mixture was then heated at 85° C. for 6 h after which time the mixture was cooled to room temperature and the solvent was removed under reduced pressure to give a yellow solid residue, which was extracted into CH$_2$Cl$_2$ (50 mL). The filtrate was concentrated to dryness to give the product as a pale yellow solid.

EXAMPLE 21

Tb(Bpz$^{12}$)$_2$(OTf)

Tb(OTf)$_3$ (1.20 g, 2.0 mmol) and KBpz$^{12}$ (2.23 g, 4.0 mmol) were suspended in THF (30 mL) and the mixture heated to reflux. After 6 h the mixture was cooled to room temperature and the solvent was removed under reduced pressure to give a yellow solid residue, which was extracted into CH$_2$Cl$_2$ (50 mL) and filtered from any insoluble residue. The filtrate was concentrated to dryness to give the product as a pale yellow solid.

EXAMPLE 22

Tb(Bpz$^{14}$)$_2$(OTf)

A mixture of Tb(OTf)$_3$ (0.61 g, 1.0 mmol) and KBpz$^{12}$ (1.11 g, 2.0 mmol) were suspended in THF (30 mL) and the mixture heated to reflux. After 7 h the mixture was cooled to room temperature and the solvent was removed under reduced pressure to give a yellow solid residue, which was extracted into CH$_2$Cl$_2$ (50 mL) and filtered from any insoluble residue. The filtrate was concentrated to dryness to give the product as a pale yellow solid (1.15 g, 86%).

What is claimed is:

1. An organometallic complex having the formula (I):

[(Z(L)$_3$)$_p$M]A$_q$     (I)

wherein Z is a carbon atom or R$^1$(B)— fragment;
p is 1,2 or 3;
q is 3-p;
A is a counterion;
R$^1$ is: (i) hydrogen, aryl or aralkyl each optionally substituted with from one to five halogen or C$_1$ to C$_6$ alkyl groups; or (ii) C$_1$ to C$_6$ alkyl, C$_1$ to C$_6$ alkenyl or C$_1$ to C$_6$ alkynyl each optionally substituted with one or more halogen atoms;
each L is covalently bound to Z and is independently selected from a group of the formula (II) or (III)

(II)

(III)

wherein R$^2$ and R$^3$ are independently selected from:
(i) halogen, cyano, nitro, sulphono, amino, C$_1$ to C$_6$ alkylamino, C$_1$ to C$_6$ alkylamido, carboxyl, C$_1$ to C$_6$ alkyloxycarbonyl, hydroxy, C$_1$ to C$_6$ alkoxy, C$_1$ to C$_6$ alkylcarbonyloxy, C$_1$ to C$_6$ alkylcarbonyl, C$_1$ to C$_6$ haloalkoxy;
(ii) aryl or aralkyl each optionally substituted on the aryl ring or, for aralkyl, on the alkylene chain with from one or more of the groups mentioned under (i) above; and
(iii) C$_1$ to C$_6$ alkenyl or C$_1$ to C$_6$ alkynyl each optionally substituted with one or more of the groups mentioned under (i) and (ii) above;
R$^2$ is —(CX$_2$)$_n$X wherein n is 0 or a positive integer from 1 to 6 and X is halogen; or
R$^2$ and R$^3$ are linked so as to form a fused aromatic or non-aromatic ring system with the pyrazolyl ring of L; and
R$^4$ is trifluoromethyl; and
M is a trivalent lanthanide metal ion.

2. An organometallic complex having the formula (I):

[(Z(L)$_3$)$_p$M]A$_q$     (I)

wherein Z is a carbon atom or R$^1$(B)— fragment;
p is 1, 2 or 3;
q is 3-p and;
A is a counterion;
R$^1$ is: (i) hydrogen, aryl or aralkyl each optionally substituted with from one to five halogen or C$_1$ to C$_6$ alkyl groups; or (ii) $C_1$ to $C_6$ alkyl, $C_1$ to $C_6$ alkenyl or $C_1$ to $C_6$ alkynyl each optionally substituted with one or more halogen atoms;

each L is covalently bound to Z and is independently selected from a group of the formula (II) or (III)

(II)

(III)

wherein $R^2$ is trifluromethyl;
$R^3$ is hydrogen; and
$R^4$ is —$(CX_2)_n X$ wherein n is 0 or a positive integer from 1 to 6 and X is halogen; or orthodihalogenated or orthodiperhalomethylated aryl, optionally further substituted on the aryl ring; and
M is a trivalent lanthanide metal ion.

3. An organometallic complex having the formula (I):

(I)

wherein Z is an $R^1(B)$— fragment;
p is 1, 2 or 3;
q is 3-p and;
A is a chloride ion;
$R^1$ is hydrogen;
each L has the formula (II) and is covalently bound to Z;

(II)

wherein $R^2$ is —$CF_3$;
$R^3$ is H; and
$R^4$ is —$CF_3$; and
M is Eu.

* * * * *

UNITED STATES PATENT AND TRADEMARK OFFICE
CERTIFICATE OF CORRECTION

PATENT NO.        : 7,601,859 B2                                              Page 1 of 1
APPLICATION NO.   : 10/848183
DATED             : October 13, 2009
INVENTOR(S)       : Victor Christou

It is certified that error appears in the above-identified patent and that said Letters Patent is hereby corrected as shown below:

IN THE CLAIMS:

In claim 2, at column 13, line 1, the subscript of "C6 alkyl, C1" should be changed to state --$C_6$ alkyl, $C_1$--.

Signed and Sealed this

Twenty-fifth Day of May, 2010

David J. Kappos
*Director of the United States Patent and Trademark Office*